Figure 1:
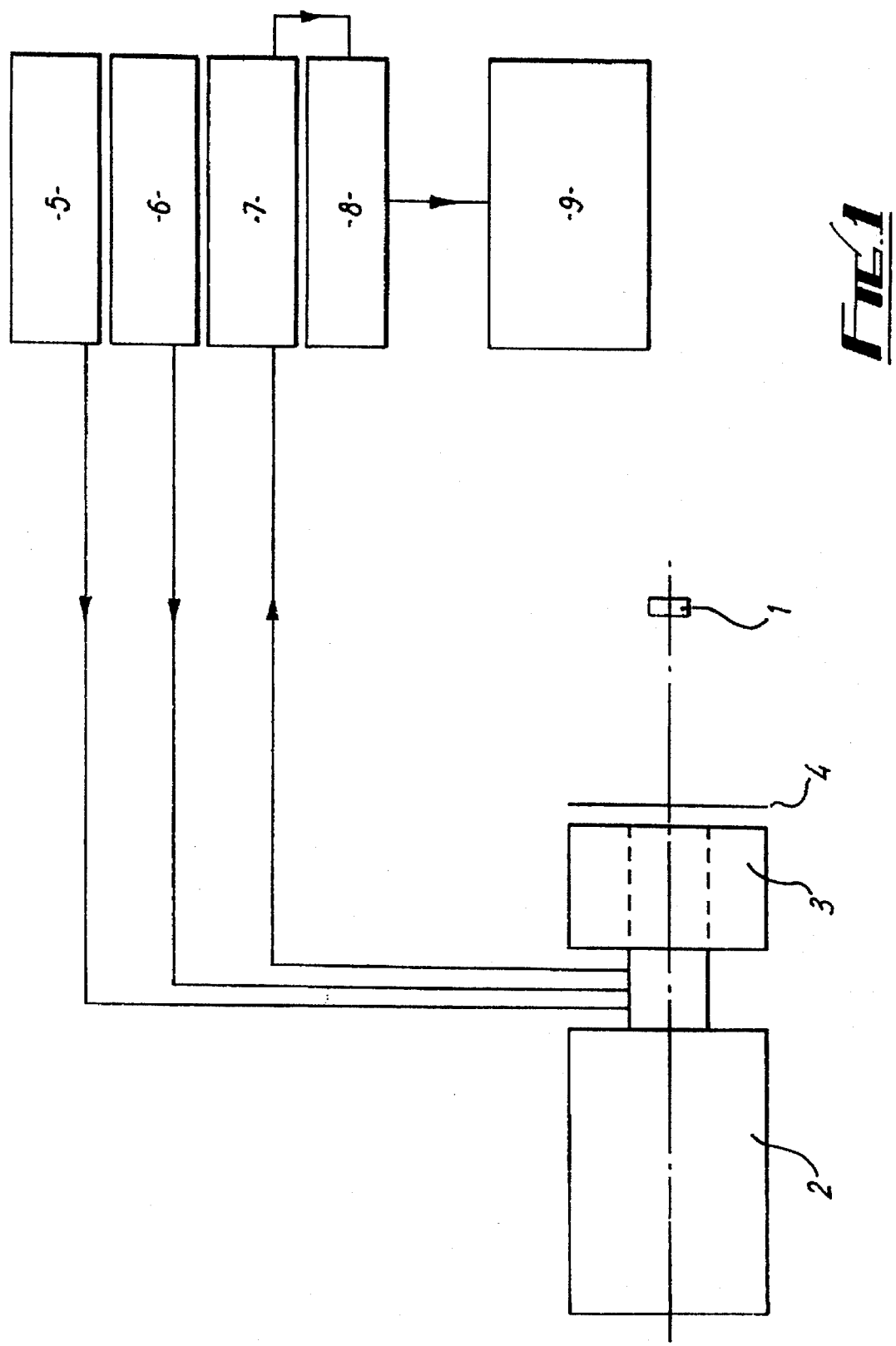

United States Patent [19]
Thornley et al.

[11] Patent Number: 5,629,525
[45] Date of Patent: May 13, 1997

[54] PLUTONIUM ASSAYING

[75] Inventors: David J. Thornley; Christopher H. Orr; Christine A. Burnett, all of Cumbria, United Kingdom

[73] Assignee: British Nuclear Fuels PLC, United Kingdom

[21] Appl. No.: 283,849

[22] Filed: Aug. 2, 1994

[30] Foreign Application Priority Data

Aug. 12, 1993 [GB] United Kingdom ............... 9316811

[51] Int. Cl.$^6$ .................................................. G01T 1/167
[52] U.S. Cl. .......................... 250/395; 250/370.03
[58] Field of Search ................... 250/395, 370.03

[56] References Cited

FOREIGN PATENT DOCUMENTS

3028218A1 2/1982 Germany.
4031249A1 4/1992 Germany.

OTHER PUBLICATIONS

T. V. Rebagay, G. A. Huff, and K. J. Hofstetter, "Automated Monitoring of In–Process Plutonium Concentration." *Anal. Chem.* vol. 54, No. 1 (Jan. 1982) pp. 8–12.

T. Dragnev and K. Schärf, "Non–destructive Gamma Spectrometry Measurement of $^{239}$Pu/$^{240}$Pu and Pu/$^{240}$Pu Ratios." *International Journal of Applied Relations and Isotopes*, vol. 26, No. 3 (Mar. 1975) pp. 125–129.

*Primary Examiner*—Constantine Hannaher
*Attorney, Agent, or Firm*—Nixon & Vanderhye

[57] ABSTRACT

A method determining the plutonium content of a material containing fluorine involves obtaining the mass ratio of plutonium in a compound comprising plutonium and fluorine, particularly plutonium tetrafluoride, to the total plutonium content. The method utilises a high resolution gamma ray spectrometry technique to obtain a count rate in a pair of gamma ray photopeaks. One of the photopeaks has an energy level of 414 keV, resulting from the decay of plutonium-239, and the other photopeak has an energy level of 583 keV, resulting from the decay of an excited sodium-22 nucleus following an (alpha,n) interaction with fluorine.

8 Claims, 1 Drawing Sheet

PLUTONIUM ASSAYING

This invention relates to the determination of the plutonium content in plutonium contaminated material containing fluorine, particularly fluorine in the form of plutonium tetrafluoride.

Fluorine is used in the process for manufacturing plutonium metal so that many waste items made from this material may contain fluorine or fluorides. When disposing of these waste items they are deposited in large drums. It is important that the plutonium content of these drums is accurately measured so that the drums can be filled to a maximum amount without exceeding the fissile limit. If the capacity of the drums is efficiently utilised a reduction in overall disposal costs can be achieved.

It has been found when using a total neutron counting technique for such measurements that the quantity of plutonium present can be overestimated due to the emission of interfering (alpha, n) reaction neutrons. The (alpha, n) neutron emission is particularly severe when the plutonium is in the form of plutonium tetrafluoride.

The assessment of plutonium content using total neutron counting requires an accurate knowledge of the specific neutron emission rate. For plutonium contained in waste material the specific neutron rate is dependent on the isotopic composition, the chemical composition and the matrix composition. The isotopic composition defines the spontaneous fission neutron rate and also the alpha emission rate which then influences the (alpha, n) reaction rates due to the chemical and matrix compositions.

The chemical composition affects the (alpha, n) neutron rate. For example, alpha interactions with fluorine produce many more neutrons than alpha reactions with oxygen. The presence of light elements, for example oxygen and fluorine, in the matrix also affects the (alpha, n) neutron rate, although to a lesser extent than their presence in the chemical composition.

The use of a conventional neutron coincidence counting technique for plutonium assaying is not considered suitable where large quantities of plutonium tetrafluoride are present. This is because the coincidence circuitry of the measuring equipment is unable to cove with very high random pulse rates and measurement precision tends to be very poor.

It is an object of this invention to provide a method of determining the plutonium content of plutonium contaminated material which overcomes the problem of overestimation caused by the presence of fluorine.

According to the present invention there is provided a method of determining the plutonium content of a material which also contains fluorine, wherein said method includes the step of determining the mass ratio of plutonium in a compound comprising plutonium and fluorine to the total plutonium content of the material using a high resolution gamma ray spectrometry technique.

In a preferred embodiment the said compound is plutonium tetrafluoride.

Preferably the method includes obtaining a count rate in a pair of gamma ray photopeaks, one of said photopeaks having an energy level of 414 keV resulting from the decay of plutonium-239, and the other of said photopeaks having an energy level resulting from the interaction of plutonium alpha particles with fluorine.

The other of said gamma ray photopeaks may have an energy level of 583 keV resulting from the decay of an excited sodium-22 nucleus following an (alpha, n) interaction with fluorine.

Preferably the photopeak having an energy level of 583 keV is corrected for thorium decay series contribution using a thorium decay series gamma ray at a 238 keV photopeak energy level.

Alternatively, the other of said gamma ray photopeaks may have an energy level of 891 keV or 1274 keV, which are unaffected by thorium decay series gamma emissions.

The invention will now be described with reference to the accompanying FIG. 1, which is a diagrammatic representation of a typical high resolution gamma spectrometry system for carrying out the invention.

A preferred method of carrying out a high resolution gamma ray technique for determining the plutonium (as fluoride) to total plutonium mass ratio is based on the following:

An (alpha, n) reaction may leave the remaining nucleus in an excited energy state. The nucleus loses this excess energy via the emission of radiation as gamma rays. Thus, (alpha, n) reactions may be identified by the detection of characteristic gamma rays.

In a material containing plutonium tetrafluoride (PuF$_4$), alpha particles of plutonium isotopes interact with fluorine atoms to produce gamma rays. The most intense gamma rays seen in the high resolution gamma spectrum are those at 583 keV and 1274 keV.

The 583 keV gamma may results from the (alpha, n) reaction:

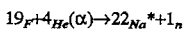

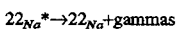

(*indicates that the nucleus is formed in an excited state of energy)

The 1274 keV gamma ray arises from two sources:

i) as a prompt gamma ray from the (alpha, p reaction:

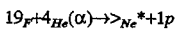

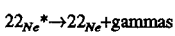

ii) as a delayed gamma ray from the de-excitation of Ne-22 following the decay of Na-22.

Plutonium-239 alpha decays spontaneously, resulting in the emission of gamma rays such as that having an energy level of 414 keV.

A relationship exists between the emission rate of the 414 keV gamma rays, the emission rate of gamma rays resulting from the interaction of alpha particles with fluorine, and the plutonium tetrafluoride to total plutonium mass ratio.

A count rate in the 414 keV photopeak (P) can be derived from:

$$P = E_{414} \cdot M \cdot B_{414} \qquad (i)$$

where:

$E_{414}$=detector efficiency at 414 keV

M=mass of plutonium $B_{414}$=414 keV gammas per second per gram of plutonium (determined from the plutonium isotopic composition).

The plutonium and americium-241 composition can be determined from a gamma spectrum obtained by high resolution gamma spectrometry during analysis or, alternatively, it can be entered separately if the isotopic composition is already known.

Note. Americium-241 is the daughter product resulting from the decay of plutonium-241 and is often present in plutonium containing material having 'grown in' with time.

A count rate in the 583 keV photopeak (F) can be derived from:

$$F = E_{583} \cdot M(PuF_4) \cdot G \cdot A \qquad \text{(ii)}$$

where:

$E_{583}$=detector efficiency at 583 keV $M(PuF_4)$=mass of plutonium tetrafluoride G=583 keV gammas per alpha (this is a constant for plutonium tetrafluoride and can be determined experimentally).

A=alphas per second per gram of plutonium tetrafluoride (determined from the plutonium and americium-241 isotopic composition).

The mass ratio (R) of plutonium tetrafluoride to total plutonium is derived from:

$$R = M(PuF_4)/M$$

and so:

$$M(PuF_4) = M \cdot R \qquad \text{(20)}$$

Incorporating this in equation (ii), F can be rewritten as:

$$F = E_{583} \cdot M \cdot R \cdot G \cdot A \qquad \text{(iii)}$$

From equations (i) and (iii), the ratio (F/P) of net counts in the 583 keV and 414 keV photopeaks is given by:

$$\begin{aligned} F/P &= E_{583} \cdot M \cdot R \cdot G \cdot A / E_{414} \cdot M \cdot B_{414} \\ &= E_r \cdot R \cdot G \cdot A / B_{414} \end{aligned}$$

and so:

$$R = (F/P) \cdot B_{414} / E_r \cdot G \cdot A \qquad \text{(iv)}$$

where $E_r$=the relative detection efficiency at 583 keV relative to that for 414 keV.

The relative efficiency is, among other things, affected by the intrinsic efficiency of the detector at 414 keV and 583 keV photopeaks. For most germanium detectors, as used in the gamma ray spectrometry technique of the present invention, the intrinsic efficiency is a defined characteristic and can be determined using known radionuclide sources.

The foregoing formula (iv) is valid when the 583 keV photopeak comprises purely $PuF_4$ (alpha, n) reaction gamma rays. Certain applications arise where the 583 keV photopeak contains a contribution from thorium-228 decay series gamma emissions. To compensate for this situation, the contribution at 583 keV from $PuF_4$ reaction gamma rays may be determined using other $PuF_4$ reaction gamma rays at energy levels of 891 keV and 1274 keV, which are unaffected by thorium decay series emissions, or by removing the thorium contribution from the 583 keV photopeak using the thorium decay series gamma ray at an energy level of 238 keV.

In general, the technique for determining the contribution of a radionuclide in one photopeak from the net photopeak count of another photopeak is as follows. The net photopeak count $C_a$, at energy $E_a$, is used to determine the net photopeak count $C_b$ from the same source at energy $E_b$. It is therefore necessary to multiply $C_a$ by the intrinsic efficiency of the detector at energy $E_b$ relative to that at energy $E_a$. This is then multiplied by the intensity of the gamma rays at energy $E_b$ relative to that for gamma rays at energy $E_a$. The intensity for a particular gamma ray emission of a particular radionuclide is defined as the number of gamma rays of that energy emitted per disintegration of that radionuclide.

This relationship is expressed as follows:

$$C_b = C_a \cdot (EFF_b / EFF_a) \cdot (I_b / I_a) \qquad \text{(v)}$$

where:

$EFF_a$ and $EFF_b$ are the intrinsic detection efficiencies at energy $E_a$ and energy $E_b$, respectively, and $I_a$ and $I_b$ are the intensities of gamma ray emissions of energy $E_a$ and energy $E_b$, respectively.

Using the general procedure described above a technique for removing the thorium decay series component from the 583 keV photopeak has been derived, as follows:

The contribution to the 583 keV photopeak from $PuF_4$ reaction gamma rays, $C_{583f}$, is determined according to the relationship:

$$C_{583f} = C_{583tot} - C_{583th} \qquad \text{(vi)}$$

where:

$C_{583tot}$ is the total photopeak count at 583 keV, and $C_{583th}$ is the thorium-228 decay series contribution.

Therefore, using formula (v) above:

$$C_{583th} = C_{238th} \cdot [EFF_{583}/EFF_{238}] \cdot [I_{583(Th-228)}/I_{238(Th-228)}] \qquad \text{(vii)}$$

where:

$C_{238th}$ is the thorium-228 decay series contribution to the 238 keV photopeak, $EFF_{238}$ and $EFF_{583}$ are the detection efficiencies at 238 keV and 583 keV, respectively, $I_{238(Th-228)}$ is the intensity of the 238 keV gamma emission from thorium-228 decay series, and $I_{583(Th-228)}$ is the intensity of the 583 keV gamma emission from thorium-228 decay series.

Therefore, substituting detector efficiency values for a particular germanium detector and available data for the gamma emission intensities, equation (vii) can be expressed as follows:

$$C_{583th} = k_1 \cdot C_{238th}$$

where:

$k_1$ is a constant appropriate for a particular germanium detector.

Assuming the 238 keV photopeak comprises only thorium series gamma rays, then:

$$C_{238th} = C_{238tot}$$

where:

$C_{238tot}$ is the total photopeak count at 238 keV. Therefore:

$$C_{583th} = k_1 \cdot C_{238tot}$$

Therefore, equation (vi), using the 583 keV photopeak with basic thorium interference correction can be expressed as follows:

$$C_{583f} = C_{583tot} - k_1 \cdot C_{238tot}$$

Similarly, using the above technique for determining the contribution of $PuF_4$ reaction gamma rays to the 583 keV photopeak using the 891 keV reaction gamma ray emission of $PuF_4$; the following equation is derived:

$$C_{583f} = [EFF_{583}/EFF_{891}] \cdot [I_{583(PuF_4)}/I_{891(PuF_4)}] \cdot C_{891}$$
$$= k_2 \cdot C_{891}$$

where:

$k_2$ is a constant appropriate for a particular germanium detector.

To determine the contribution of the $PuF_4$ reaction gamma rays to the 883 keV photopeak using the 1274 keV reaction gamma ray emission of $PuF_4$, separate formulae have been derived for $PuF_4$ which has existed for over 10 years and for fresh $PuF_4$. These formulae are of the same general form, but have different values of constants since the intensity of the 1274 keV gamma emission varies with time until equilibrium is reached after about 10 years.

For fresh $PuF_4$ samples, equation (v) may be written:

$$C_{583f} = C_{1274} \cdot [EFF_{583}/EFF_{1274}] \cdot [I_{583(PuF_4)}/I_{1274(PuF_4)F}] \quad \text{(viii)}$$

where:

$I_{1274(PuF_4)F}$ is the intensity for the 1274 reaction gamma ray emission for freshly prepared $PuF_4$.

Therefore, substituting germanium detector efficiency values and available data for gamma emission intensities, equation (viii) can be expressed as follows:

$$C_{583f} = k_3 \cdot C_{1274}$$

where:

$k_3$ is a constant appropriate for a particular germanium detector.

For $PuF_4$ which has existed for over 10 years, equation (v) may be written:

$$C_{583f} = C_{1274} \cdot [EFF_{583}/EFF_{1274}] \cdot [I_{583(PuF_4)}/I_{1274(PuF_4)A}] \quad \text{(ix)}$$

where:

$I_{1274(puF_4)A}$ is the intensity for the 1274 keV reaction gamma ray emission for $PuF_4$ of more than 10 years old.

Therefore, substituting detector efficiency values and available data for gamma emission intensities, equation (ix) can be written:

$$C_{583f} = k_4 \cdot C_{1274}$$

where:

$k_4$ is a constant appropriate for a particular germanium detector.

For some plutonium samples to be analysed the 238 keV photopeak may contain a contribution from plutonium-239 which is significant compared to the contribution from thorium-228 decay series gamma rays. There is also a minor plutonium-239 contribution to the 583 keV photopeak.

The contribution of $PuF_4$ reaction gamma rays to the 583 keV photopeak from $PuF_4$ gamma spectrum, $C_{583f}$, is as follows:

$$C_{583f} = C_{583} - C_{583th} - C_{583(Pu-239)} \quad \text{(x)}$$

where:

$C_{583}$ is the net count for the 583 keV photopeak $C_{583th}$ is the thorium-228 decay series contribution to the 583 keV photopeak, and $C_{583(Pu-239)}$ is the plutonium-239 contribution to the 583 keV photopeak.

Each of the $C_{583th}$ and $C_{583(Pu-239)}$ terms can be evaluated using the aforementioned general formula (v). Substituting the values obtained in formula (x) the following formula is derived:

$$C_{583f} = C_{583} - [EFF_{583} \cdot I_{583(Th-228)}] \cdot C_{238} \quad \text{(xi)}$$
$$[EFF_{238} I_{238(Th-228)}] +$$
$$EFF_{583}[I_{238(Pu-239)} \cdot I_{583(Th-228)} - I_{583(Pu-239)}] \cdot C_{414}$$
$$EFF_{414}[I_{414(Pu-239)} I_{238(Th-228)} I_{414(Pu-239)}]$$

where:

$C_{583}$, $C_{238}$ and $C_{414}$ are the net counts for the 583 keV, 238 keV and 414 keV photopeaks, respectively.

$EFF_{583}/EFF_{238}$ is the detection efficiency ratio for gamma rays at 583 keV relative to that for 238 keV gamma rays.

$EFF_{583}/EFF_{414}$ is the detection efficiency ratio for gamma rays at 583 keV relative to that for 414 keV gamma rays.

$I_{583(Th-228)}/I_{238(Th-228)}$ is the intensity ratio of 583 keV, Th-228 decay series gamma rays relative to that for 238 keV, Th-228 decay series gamma rays.

$I_{238(Pu-239)}/I_{414(Pu-239)}$ is the intensity ratio of 238 keV, Pu-239 decay series gamma rays relative to that for 414 keV, Pu-239 decay series gamma rays.

$I_{583(Th-228)}/I_{238(Th-228)}$ is the intensity ratio of 583 keV, Th-228 decay series gamma rays relative to that for 238 keV, Th-228 decay series gamma rays.

$I_{583(Pu-239)}/I_{414(Pu-239)}$ is the intensity ratio of 583 keV, Pu-239 decay series gamma rays relative to that for 414 keV, Pu-239 decay series gamma rays.

Formula (xi) can be rewritten in the following way:

$$C_{583f} = C_{583} - k_5 \cdot C_{238} + k_6 \cdot C_{414}$$

where:

$k_5$ and $k_6$ are constants which are appropriate for the particular germanium detected used.

In practice, the plutonium tetrafluoride measurements are carried out using a high resolution gamma spectrometry system, a typical representation of which is shown in FIG. 1. A sample 1 containing plutonium tetrafluoride is placed in front of and on the germanium crystal axis of a high purity germanium detector 2. The item to be analysed may range from a small sample, as shown, to a large container holding intermediate level radioactive waste containing plutonium. To reduce interference from background radiation the detector 2 is equipped with a lead collimator 3. A thin cadmium shield 4 is placed between the sample 1 and the detector 2 to reduce the effects of high intensity, low energy gamma radiation.

A high voltage power supply unit 5 and a preamplifier power supply 6 are connected to the detector 2. Output signals from the detector 2 are transmitted to a spectroscopic amplifier 7 from which the output signals are directed to an analogue-to-digital converter 8. Digital signals from the converter 8 are processed by a personal computer and multi-channel analyser system 9 which is equipped with software suitable for analysing plutonium tetrafluoride.

In use, the system shown in FIG. 1 is operated so that a gamma spectrum is collected of the radiation emitted by the sample 1 by the multi-channel analyser system 9. The relevant net photopeak counts are obtained from the gamma spectrum by the analyser system 9 and used to determine the plutonium and americium isotopic composition of the sample. From this information, the mass ratio of the plutonium tetrafluoride to the total plutonium content is subsequently obtained using the formulae, as disclosed earlier in the specification, which are incorporated in the computer software program. The analysis can be carried out by inputting data into the program manually, or by netting up the system to carry out the analysis automatically.

The technique can be incorporated as an integral part of a complete measurement system as, for example, in a drum assay system, or it can be implemented using portable equipment and employed to assay in a wide variety of situations. Examples range from scrapings from glovebox walls taken during decommissioning procedures through to in situ analysis of large items such as crates or drums holding intermediate level radioactive waste containing plutonium. By obtaining an accurate measurement of the plutonium content of the waste material and drums enables the drums to be filled to a capacity up to the fissile limit without exceeding it. This results in the drums being filled to their optimum capacity, so reducing the cost of disposal.

The foregoing techniques for analysing the gamma spectrum to give a measurement of the plutonium (as fluoride) to total plutonium mass ratio is quick and easy to carry out. It can be used in combination with total neutron counting in situations which cannot be dealt with satisfactorily by conventional techniques, such as total neutron counting alone or neutron coincidence counting. In the presence of plutonium tetrafluoride these conventional techniques result in large overestimates of the amount of plutonium present, so incurring excessive storage costs and possibly giving rise to perceived criticality safety problems when in actuality no such criticality hazard exists.

We claim:

1. A method of determining the plutonium content of a material which also contains fluorine, wherein said method comprises the steps of:

(a) obtaining by high resolution gamma ray spectrometry a count rate in a pair of gamma ray photopeaks; and thereafter, (b) determining the mass ratio of plutonium in a compound comprising plutonium and fluorine to the total plutonium content of the material utilizing said count rate.

2. A method as claimed in claim 1, wherein said compound is plutonium tetrafluoride.

3. A method as claimed in claim 1, wherein one of said gamma ray photopeaks has an energy level of 414 keV resulting from the decay of plutonium-239, and the other of said gamma ray photopeaks has an energy level of 583 KeV resulting from the interaction of plutonium alpha particles with fluorine.

4. A method as claimed in claim 1, wherein said gamma ray photopeak having an energy level of 583 keV results from the decay of an excited sodium-22 nucleus following an (alpha,n) interaction with fluorine.

5. A method as claimed in claim 4, wherein the count rates obtained are substituted in a formula for calculating the mass ratio (R) of plutonium tetrafluoride to the total plutonium content of the material, said formula being $$R=(F/P) \cdot B_{414}/Er \cdot G \cdot A$$

where

F=count rate in the 583 keV photopeak

P=count rate in the 414 keV photopeak $B_{414}$=the 414 keV gamma per second per gram of plutonium (determined from the plutonium isotopic composition)

Er=the relative detection efficiency at 583 keV relative to that for 414 keV

G=the 583 keV gammas per alpha (a constant for plutonium tetrafluoride, determined experimentally)

A=the alphas per second per gram of plutonium tetrafluoride (determined from the plutonium and americium-241 isotopic composition).

6. A method as claimed in claim 4, wherein the photopeak having an energy level of 583 keV is corrected for thorium decay series contribution using a thorium decay series gamma ray at a 238 keV photopeak energy level.

7. A method as claimed in claim 1, wherein the other of said gamma ray photopeaks has an energy level of 891 keV which is unaffected by thorium decay series gamma emissions.

8. A method as claimed in claim 1, wherein the other of said gamma ray photopeaks has an energy level of 1274 keV which is unaffected by thorium decay series gamma emissions.

* * * * *